US005728110A

United States Patent [19]

Vidal et al.

[11] Patent Number: 5,728,110

[45] Date of Patent: Mar. 17, 1998

[54] PROCEDURE FOR USE OF LAPAROSCOPIC SURGICAL INSTRUMENTS

[75] Inventors: Claude A. Vidal, Santa Barbara; Russell J. Redmond, Goleta; Alan K. Plyley, Santa Barbara, all of Calif.

[73] Assignee: United States Surgical Corporation, Norwalk, Conn.

[21] Appl. No.: 802,886

[22] Filed: Feb. 18, 1997

Related U.S. Application Data

[60] Continuation of Ser. No. 458,170, Jun. 2, 1995, abandoned, which is a division of Ser. No. 55,817, Apr. 30, 1993, Pat. No. 5,447,265.

[51] Int. Cl.$^6$ .......... A61B 17/00

[52] U.S. Cl. .......... 606/143; 606/151; 128/898; 227/19; 227/175.1

[58] Field of Search .......... 606/143, 151, 606/142, 139; 227/19, 175.1–182.1; 128/898

[56] References Cited

U.S. PATENT DOCUMENTS

| | | |
|---|---|---|
| 3,692,224 | 9/1972 | Astafiev et al. . |
| 4,086,926 | 5/1978 | Green et al. . |
| 4,202,480 | 5/1980 | Annett . |
| 4,256,251 | 3/1981 | Moshofsky . |
| 4,391,401 | 7/1983 | Moshofsky . |
| 4,519,532 | 5/1985 | Foslien . |
| 4,520,817 | 6/1985 | Green . |
| 4,527,724 | 7/1985 | Chow et al. . |
| 4,569,346 | 2/1986 | Poirier . |
| 4,576,167 | 3/1986 | Noiles . |
| 4,607,636 | 8/1986 | Kula et al. . |
| 4,608,981 | 9/1986 | Rothfuss et al. . |
| 4,633,874 | 1/1987 | Chow et al. . |
| 4,646,745 | 3/1987 | Noiles . |
| 4,809,898 | 3/1989 | Grassner et al. . |
| 4,863,088 | 9/1989 | Redmond et al. . |
| 4,869,415 | 9/1989 | Fox . |
| 4,892,244 | 1/1990 | Fox et al. . |
| 4,938,408 | 7/1990 | Bedi et al. . |
| 4,941,623 | 7/1990 | Pruitt . |
| 4,955,959 | 9/1990 | Thompkins et al. . |
| 5,040,715 | 8/1991 | Green et al. . |
| 5,071,052 | 12/1991 | Rodak et al. . |

(List continued on next page.)

FOREIGN PATENT DOCUMENTS

| | | |
|---|---|---|
| 5476486 | 9/1986 | Australia . |
| 5476586 | 9/1986 | Australia . |
| 2082229 | 5/1993 | Canada . |
| 0324638 | 7/1989 | European Pat. Off. . |
| 0373762 | 6/1990 | European Pat. Off. . |
| 0399701 | 11/1990 | European Pat. Off. . |
| 0484677 | 5/1992 | European Pat. Off. . |
| 0489436 | 6/1992 | European Pat. Off. . |
| 0503662 | 9/1992 | European Pat. Off. . |
| 0514139 | 11/1992 | European Pat. Off. . |
| 0537572 | 4/1993 | European Pat. Off. . |
| 0545029 | 6/1993 | European Pat. Off. . |
| 0552423 | 7/1993 | European Pat. Off. . |
| 0579038 | 1/1994 | European Pat. Off. . |
| 0598202 | 5/1994 | European Pat. Off. . |
| WO83/02247 | 7/1983 | WIPO . |
| WO92/10976 | 7/1992 | WIPO . |

OTHER PUBLICATIONS

Flickinger et al. Surgical Stapling Gastric and Small Bowel Procedures, vol. 1, pp. 1–145, 1988.

*Primary Examiner*—Jeffrey A. Schmidt

[57] ABSTRACT

A laparoscopic stapler with a blocking body is disclosed. The blocking body allows the stapler to be inserted into the abdominal cavity through a cannula and removed therefrom until the staples are fired. When the staples are fired, the blocking body allows the stapler to be removed from the abdominal cavity of the patient through the cannula. After the staples have been fired and the stapler is removed from the abdominal cavity, the blocking body is in a blocking position where it then prevents the stapler from being reinserted through the cannula.

10 Claims, 11 Drawing Sheets

U.S. PATENT DOCUMENTS 5,071,430 12/1991 de Salis et al. .
5,084,057 1/1992 Green et al. .
5,100,420 3/1992 Green et al. .
5,106,008 4/1992 Tompkins et al. .
5,122,122 6/1992 Allgood .
5,129,885 7/1992 Green et al. .
5,170,925 12/1992 Madden et al. .
5,171,247 12/1992 Hughett et al. .
5,171,249 12/1992 Stefanchik et al. .
5,174,487 12/1992 Rothfuss et al. .
5,176,695 1/1993 Dulebohn .
5,220,928 6/1993 Oddsen et al. .
5,253,793 10/1993 Green et al. .
5,275,323 1/1994 Schulze et al. .
5,307,976 5/1994 Olson et al. .
5,318,221 6/1994 Green et al. .
5,332,142 7/1994 Robinson et al. .
5,336,232 8/1994 Green et al. .
5,447,265 9/1995 Vidal et al. .

Fig. 19
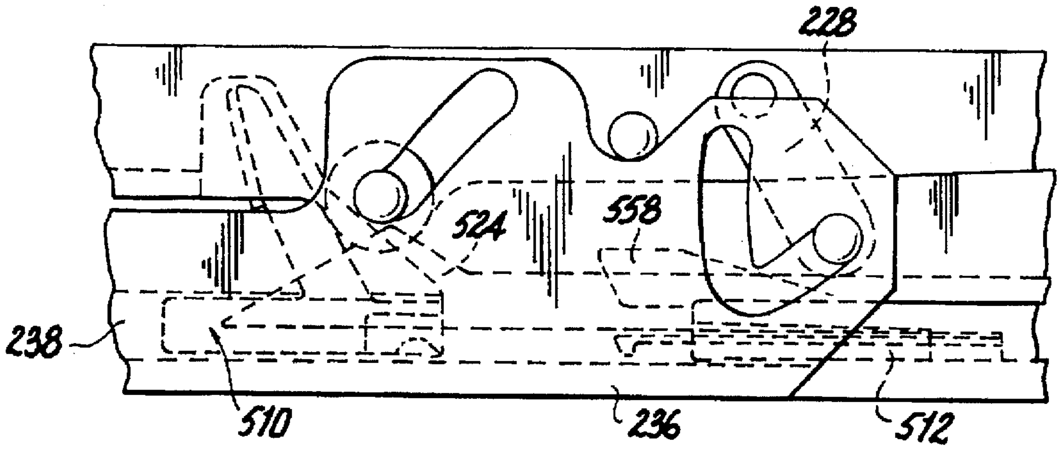
Fig. 20
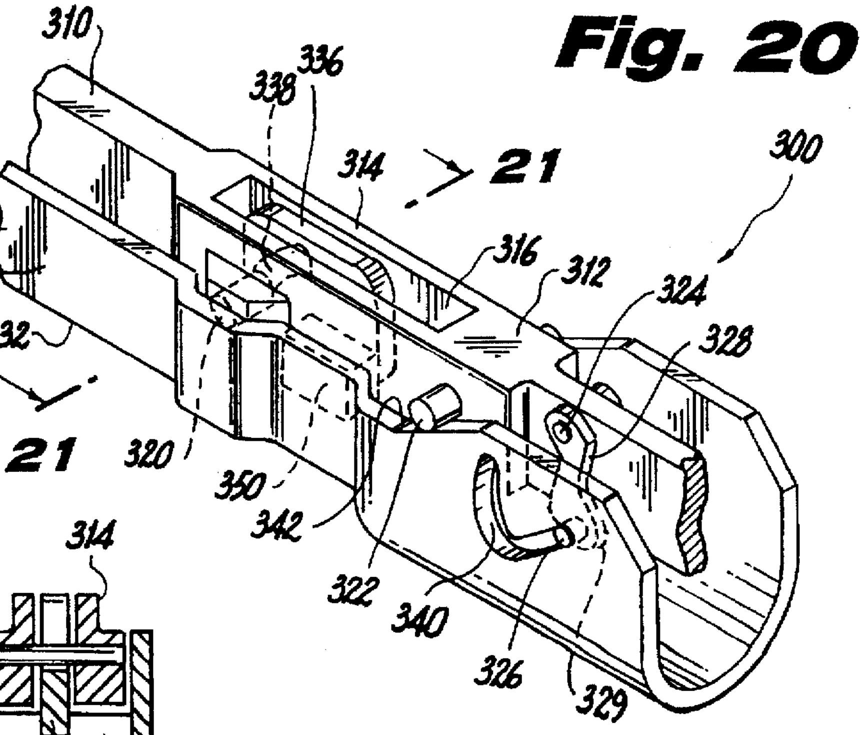
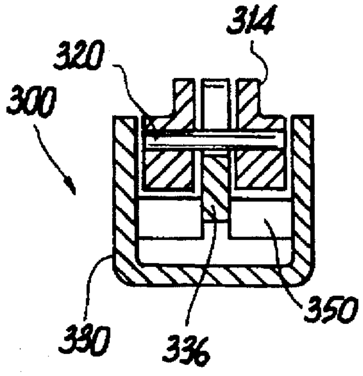
Fig. 21

Fig. 23
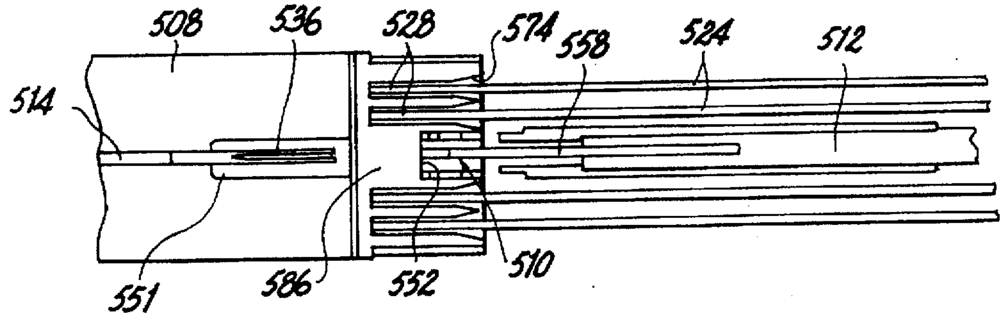
Fig. 24
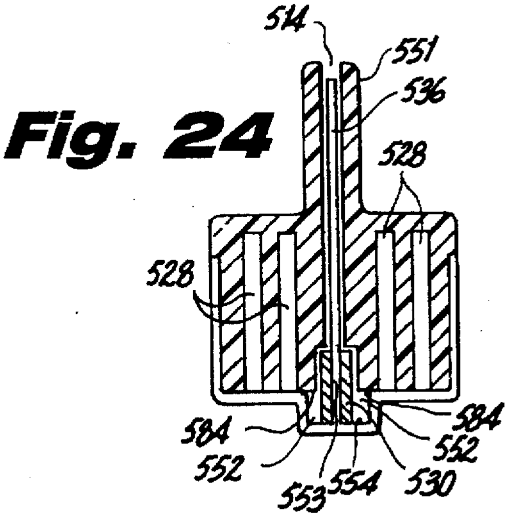
Fig. 25
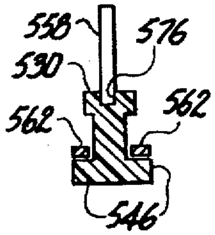
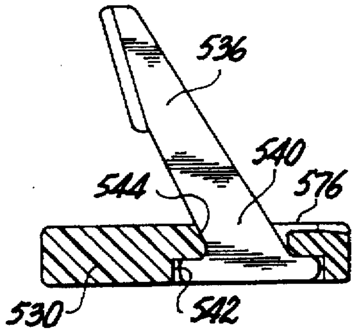
Fig. 26
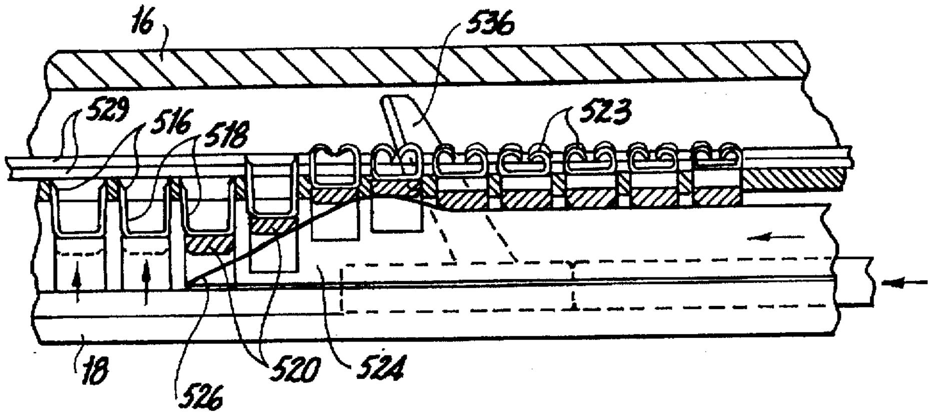
Fig. 27

PROCEDURE FOR USE OF LAPAROSCOPIC SURGICAL INSTRUMENTS

This is a continuation of application Ser. No. 08/458,170 filed on Jun. 2, 1995 now abandoned which is a division of Ser. No. 08/055,817 filed Apr. 30, 1993 now U.S. Pat. No. 5,447,765.

TECHNICAL FIELD

The present invention is directed to surgical instruments that are inserted through a trocar cannula during a laparoscopic surgical procedure.

BACKGROUND

A large number of abdominal surgical procedures are performed with laparoscopic techniques in order to avoid a large skin incision. Typically in laparoscopic surgery, a special needle (e.g. a needle similar to the needles described in U.S. Pat. No. 4,808,168 and U.S. patent application Ser. No. 07/808,152) is inserted through the skin, and used to pressurize the abdominal cavity with an insufflating gas such as carbon dioxide ($CO_2$).

Once the abdomen is adequately dilated, the needle is removed and a rigid access tube or cannula with a diameter larger than the pneumoneedle (for example 5, 10 or 11 mm) is passed through the skin in generally the same location. To drive the cannula through the skin, the surgeon places a trocar in the lumen of the cannula to provide a sharp, leading edge for cutting tissue. The art is replete with trocar and cannula assemblies, including those shown in U.S. Pat. Nos. 4,535,773, 4,601,710, 4,654,030, 4,902,280, 4,931,042, 5,104,382, 5,116,353 and 5,152,754 the entire contents of which are herein expressly incorporated by reference.

The cannula provides access for laparoscopic surgical tools or instruments such as a tissue tacker, a stapler or a surgical clip applier. Such instruments include mechanical tissue engagement devices such as tissue tackers, staples and clips. Examples of such surgical instruments are described in U.S. Pat. Nos. 5,040,715, 5,084,057, 5,100,420, 5,171,247, 5,171,249, 5,174,487 and 5,176,695 (the entire contents of each of which are herein expressly incorporated by reference).

It may be difficult to determine whether the supply of tissue engagement devices in an existing surgical instrument is depleted (e.g. whether the instrument is spent), particularly during a laparoscopic surgical procedure where a surgeon's attention may be focused elsewhere. U.S. Pat. Nos. 5,084,057 and 5,171,247 disclose laparoscopic clip appliers which have devices which address this problem. However, valuable time during the laparoscopic surgical procedure may be wasted by inserting a spent surgical instrument through the cannula.

A surgical instrument such as a laparoscopic surgical stapler has jaws for clamping on tissue. If the jaws are clamped on tissue when the supply of staples is depleted, the tissue may suffer unnecessary tissue trauma. Further, a laparoscopic stapler typically has knife which is intended to cut between rows of applied staples. If the staples are not present and the stapler is fired, the knife blade may cut tissue that is intended to be closed by the missing staples, clearly an undesirable result.

BRIEF DESCRIPTION OF THE INVENTION

According to the present invention there is provided a laparoscopic surgical instrument adapted to be inserted through a cannula and into the abdominal cavity of a patient during a laparoscopic surgical procedure. The laparoscopic surgical instrument includes a blocking body that prevents the surgical instrument from being reinserted into the abdominal cavity after tissue engagement devices (such as staples, clips or tissue tackers) within the surgical instrument are spent.

The blocking body allows the spent surgical instrument to be removed from the abdominal cavity through the cannula, but thereafter prevents the instrument from being reinserted through the cannula. Valuable time during the laparoscopic procedure is not wasted by inadvertently or accidentally inserting a spent instrument through the cannula, and tissue is not unnecessarily traumatized.

According to the present invention, there is provided a laparoscopic surgical instrument such as a stapler comprising a proximal portion, a distal portion having at least one mechanical tissue engagement device (such as staples), actuation means for placing the staples on tissue, an elongate, substantially cylindrical shaft portion between the proximal and distal portions for abutment with inner surfaces of the cannula when the stapler within the cannula, and the blocking body.

The stapler also comprises a means, operatively associated with the actuation means, which mounts the blocking body for pivotal movement between a non-blocking position which affords insertion and removal of the distal portion through the cannula, and an insertion blocking position in which the blocking body affords removal of the distal portion from the abdominal cavity, and in which the blocking body thereafter prevents insertion of the distal portion through the cannula. The stapler also preferably comprises biasing means, such as a spring, for urging the blocking body toward the blocking position.

In a preferred embodiment of the present invention, the means mounting the blocking body for movement between non-blocking and insertion blocking positions comprises the distal portion having a latch, and the blocking body having pin for engaging the latch when the blocking body is in the non-blocking position. Also preferably, the blocking body comprises a cam surface for engaging the end of the cannula to afford removal of the distal portion from the abdominal cavity through the cannula when the blocking body is in the blocking position, and an obstruction surface for engaging the cannula to prevent the surgical instrument from being reinserted through the cannula.

The present invention may also be described as a laparoscopic surgical procedure comprising the steps of: (1) providing a cannula, (2) inserting a portion of the cannula into the abdominal cavity of a patient, (3) providing a laparoscopic instrument having a distal portion with at least one mechanical tissue engagement device, an actuation means capable of engaging the mechanical tissue engagement device on tissue, and a blocking body movable between blocking and non-blocking positions, (4) inserting the distal portion of the laparoscopic surgical instrument into the abdominal cavity of the patient through the cannula, (5) actuating the actuation means until no mechanical tissue engagement device remains to be engaged on tissue, and then (6) removing the distal portion from the abdominal cavity such that, after the distal portion is removed, the blocking body is in the blocking position in which it thereafter prevents insertion of the distal portion through the cannula.

BRIEF DESCRIPTION OF THE DRAWINGS

The present invention will be further described with reference to the accompanying drawing wherein like reference numerals refer to like parts in the several views, and wherein:

FIG. 19 is an enlarged side view of a portion of the surgical instrument shown in FIG. 18, and showing a knife assembly and a knife actuating assembly.

FIG. 20 is a partial perspective view of a third modified surgical instrument having an articulated jaw structure.

FIG. 21 is a rear sectional view of the surgical instrument shown in FIG. 20 taken along line 21—21.

FIG. 23 is a top view of the knife assembly and the knife actuating assembly shown in FIG. 22A.

FIG. 24 is a sectional view taken along line A—A in FIG. 22C.

FIG. 25 is a sectional view taken along line B—B in FIG. 22C.

FIG. 26 is an enlarged sectional view of the knife assembly.

FIG. 27 is a side sectional view of a surgical stapler, showing the stapling and cutting of tissue between the jaws of the stapler.

FIGS. 29 and 30 sequentially illustrate the operation of the blocking body according to the present invention in a laparoscopic surgical stapler wherein:

FIG. 29 is a schematic side view which illustrates the blocking body in a non-blocking position, and a latch in a latching position; and FIG. 30 is a schematic side view which illustrates the blocking body in an insertion blocking position, and a latch in an unlatched position.

DETAILED DESCRIPTION

Figure 1:
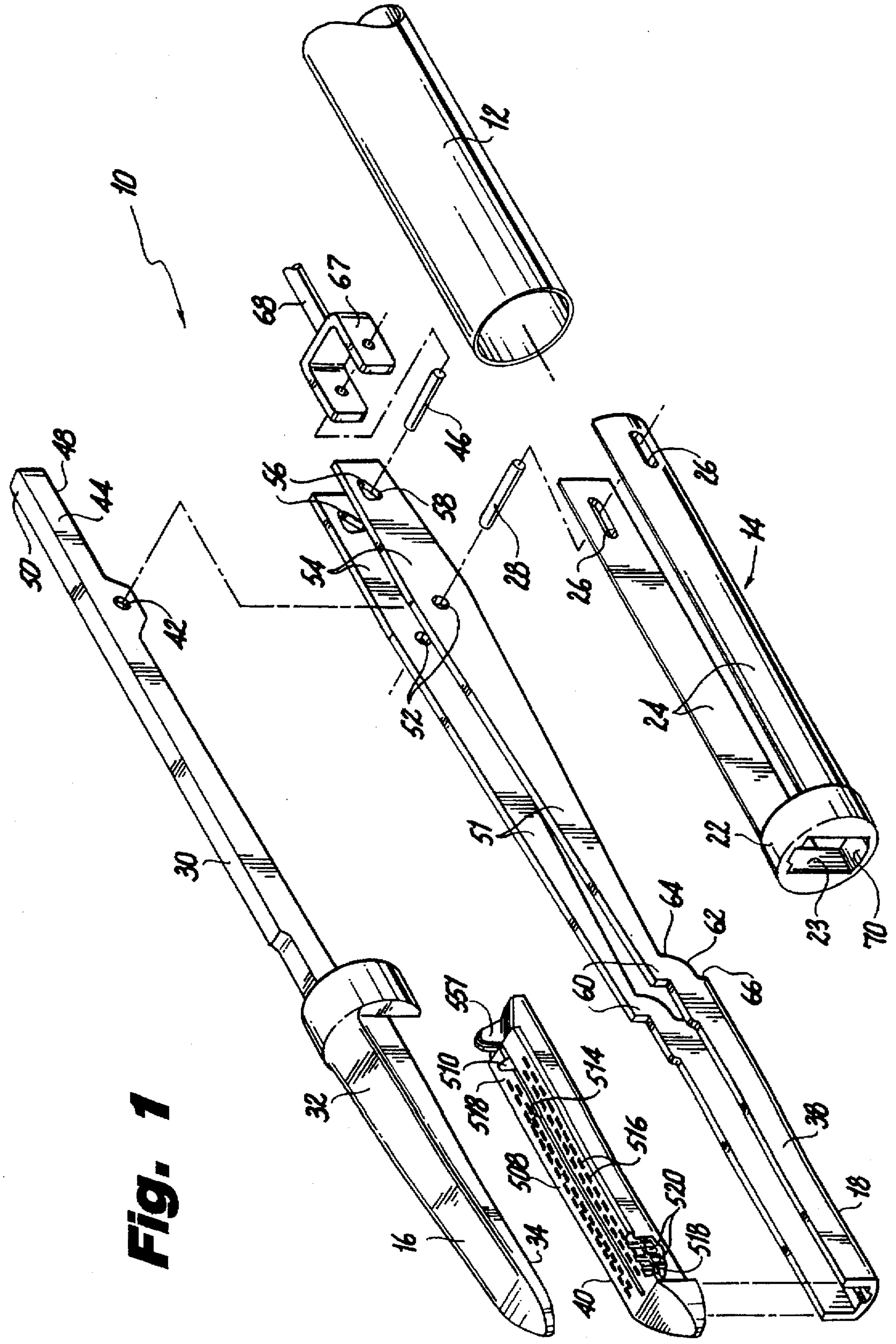
FIG. 1 is an exploded perspective view of a surgical instrument having an articulated jaw structure.

A preferred surgical instrument 10 with articulated jaw structure is shown in pertinent part in FIGS. 1–12. Only the distal end of the instrument is shown, it being appreciated that the surgical instrument may be actuated using structure and techniques well known to those skilled in the art.

The surgical instrument 10 includes a tubular frame 12, a first or upper jaw 16 and a second or lower jaw 18. In surgical stapling apparatus, one of the jaws (in this case, the lower jaw), may include a disposable staple cartridge 508. The tubular frame preferably includes a collar 14. Both the frame and collar are preferably made of stainless steel. The collar has an end portion 22 defining an opening 23 therethrough for receiving the jaws. A pair of diametrically opposed arms 24 extend axially from the end portion into the interior of the tubular frame. Each arm defines an axially extending slot 26. A collar pin 28 is disposed and located by the slots 26 such that the collar pin extends transversely across the tubular frame. The arms of the collar form a relatively tight fit against the interior surface of the tubular frame. A proximal end (not shown) of the tubular frame is mounted to the surgical instrument by methods well known to those skilled in the art.

The upper jaw 16 has a proximal portion 30 received in the tubular frame and a distal portion 32 that extends out of the end portion 22 of the collar 14. The distal portion of the upper jaw has a tissue contacting surface 34. Similarly, the lower jaw 18 has a proximal portion 36 received in the tubular frame and a distal portion 38 that extends out of the end portion 22 of the collar 14. The upper surface of the disposable staple cartridge 508 has a tissue contacting surface 40.

The jaws are pivotally mounted to each other such that in an approximated position (FIG. 4), the tissue contacting surfaces are in opposed relationship to each other. The proximal portion 30 of the upper jaw 16 is a longitudinally extending bar that defines a transverse opening 42 for closely receiving the collar pin 28 located by the collar 14. A proximal end 44 of the upper jaw is located by a cam 46. The cam is preferably a pin that is disposed parallel to the collar pin 28, transversely across the tubular frame. The cam 46 engages a lower camming surface 48 of the proximal end of the upper jaw. The inside surface of the tubular frame engages an upper surface 50 of the proximal end of the upper jaw such that the tubular frame, the collar pin and the cam vertically locate the upper jaw.

Figure 6:
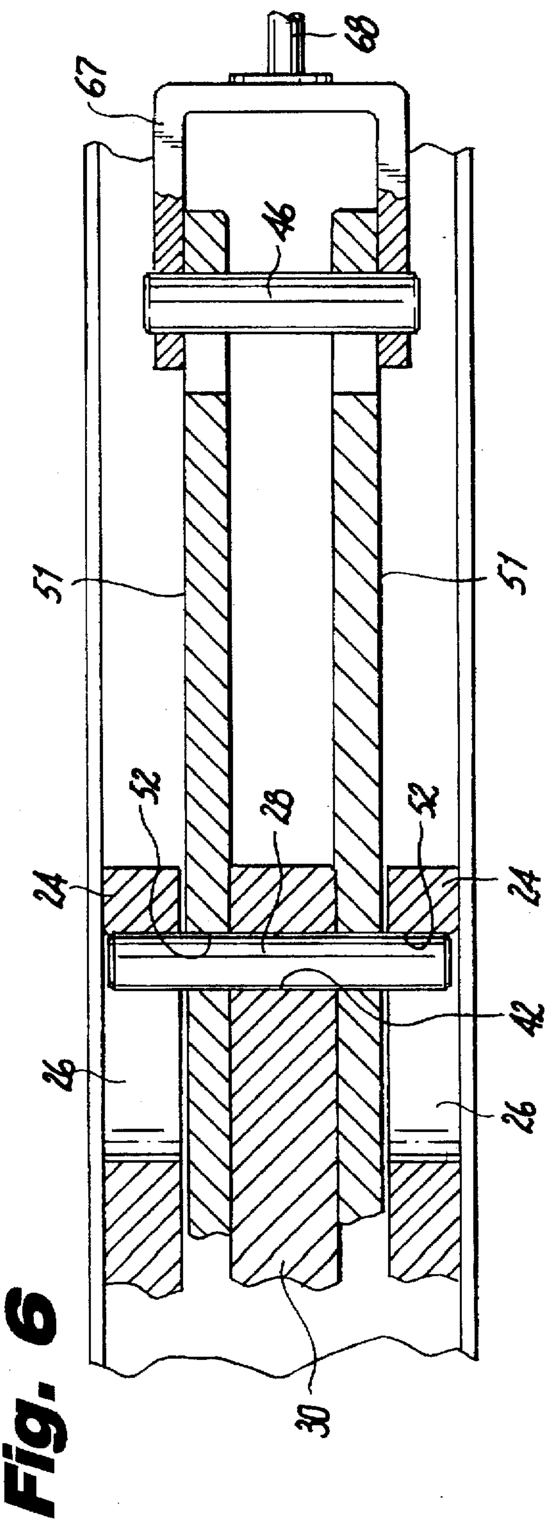
FIG. 6 is a top sectional view of the surgical instrument shown in FIG. 4, taken along line 6—6.
Figure 7:
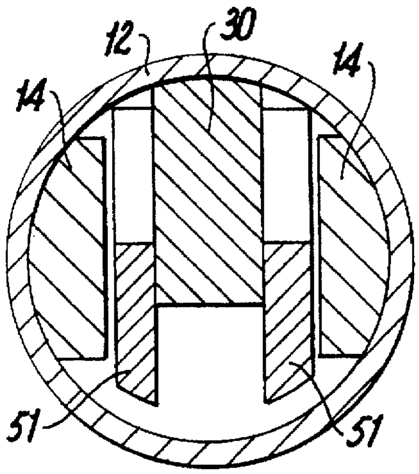
FIG. 7 is a front sectional view of the surgical instrument shown in FIG. 2, taken along line 7—7.
Figure 8:
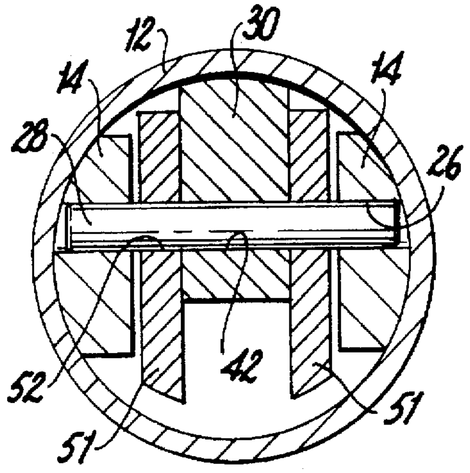
FIG. 8 is a front sectional view of the surgical instrument shown in FIG. 2, taken along line 8—8.
Figure 9:
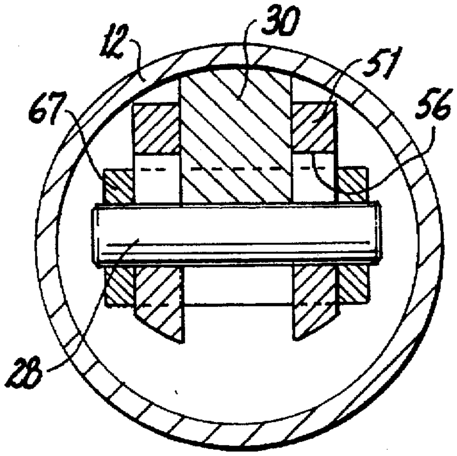
FIG. 9 is a front sectional view of the surgical instrument shown in FIG. 2, taken along line 9—9.
Figure 10:
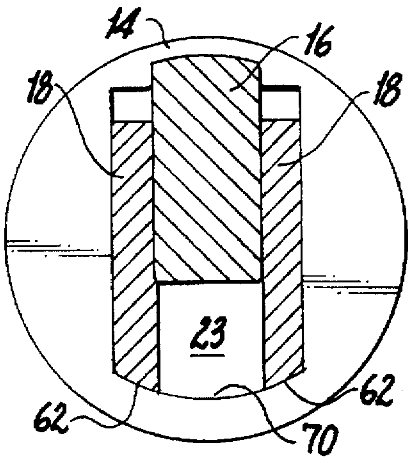
FIG. 10 is a front sectional view of the surgical instrument shown in FIG. 3, taken along line 10—10.

The proximal portion 36 of the lower jaw 18 is a pair of longitudinally extending members 51 that are located on each side, respectively, of the proximal portion 30 of the upper jaw (see FIGS. 6 and 7). Each member 51 defines a transverse opening 52 for closely receiving the collar pin 28 located by collar 14. The collar pin 28 provides an axis about which the lower jaw may pivot with respect to the upper jaw (see FIGS. 6 and 8). A proximal end 54 of each member 51 of the lower jaw defines a ramped slot 56 that receives the cam 46 (see FIGS. 1, 6 and 9). The cam engages diagonally extending camming surfaces 58 of the ramped slots. Each diagonally extending camming surface extends downwardly from the proximal end of the slot to the distal end of the slot (see FIG. 3). Each of the longitudinally extending members 51 of the lower jaw, at distal ends 60 thereof, defines a ramp 62. An upper portion 64 of each ramp is curved. Below each ramp is a shoulder 66.

The cam 46 may be fixed to a clevis 67 that is mounted to the distal end of an actuating rod 68. Preferably, the actuating rod is axially moveable within the tubular frame to move the cam between first, second and third positions to be described in more detail below. A proximal end (not shown) of the actuating rod is connected to the surgical instrument by methods known to those skilled in the art for actuation by the operator of the instrument.

Figures 2, 3, 4:
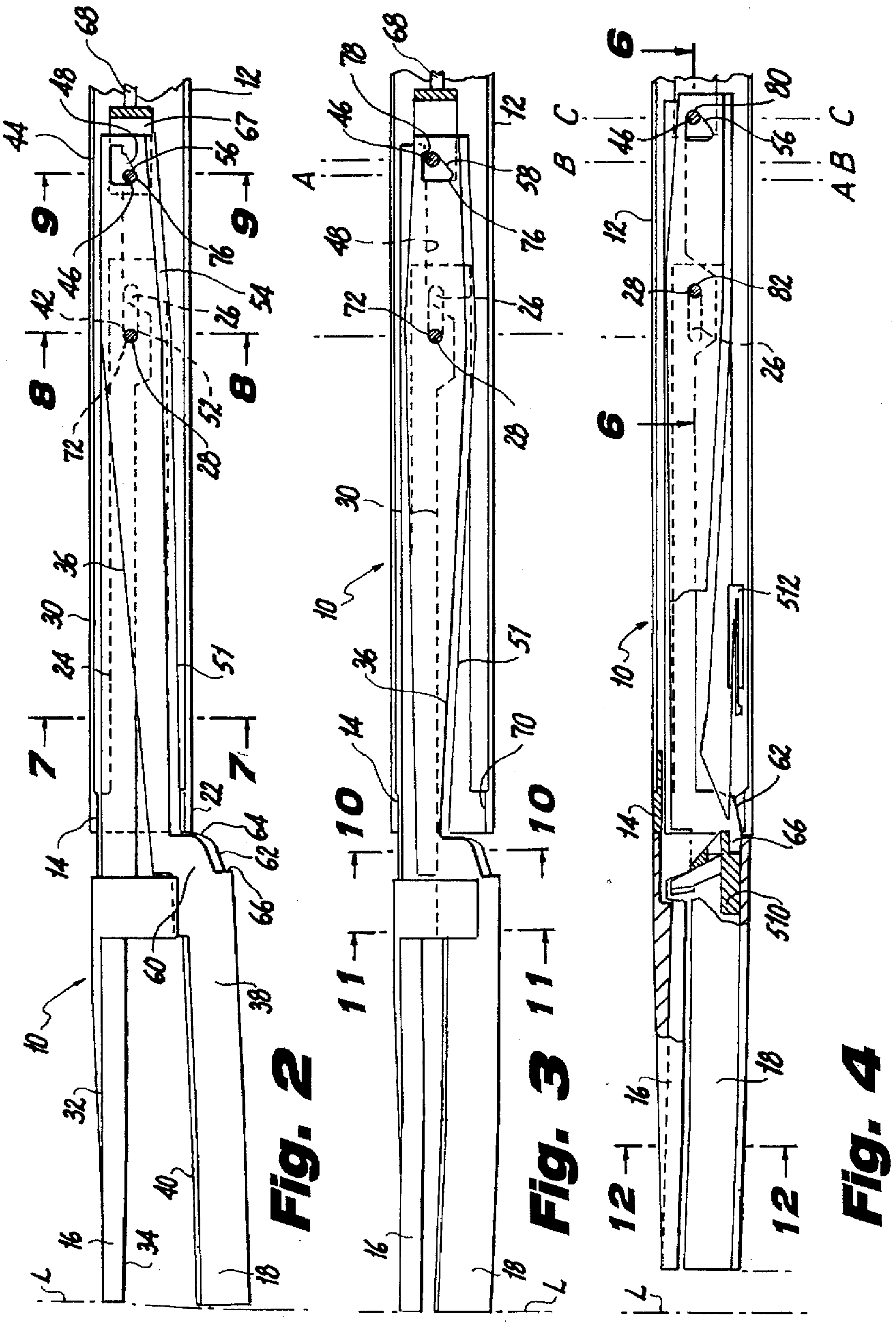
FIG. 2 is an assembled side view of the surgical instrument shown in FIG. 1, showing the jaws in a fully open position.
FIG. 3 is an assembled side view of the surgical instrument shown in FIG. 1, showing the jaws in an intermediate position.
FIG. 4 is an assembled side view of the surgical instrument shown in FIG. 1, showing the jaws in an approximated position, and showing a knife assembly and a knife actuating assembly.

With reference now to FIGS. 2–4, the operation of the jaw structure of the surgical instrument will be described. FIG. 2 shows the jaws in a fully open position with the cam 46 in a first position A. In the open position, the distal portions 32, 38 of the jaws are fully extended from the tubular member with the curved upper portion 64 of the ramp of the lower jaw adjacent to the end portion 22 of the collar 14. The collar pin 28 is in a first position at a distal end 72 of the collar arm slots 26. The cam 46 is between the lower camming surface 48 of the upper jaw and a lower end 76 of the ramped slot 56, preventing counterclockwise rotation of the lower jaw about the collar pin 28.

Figure 11:
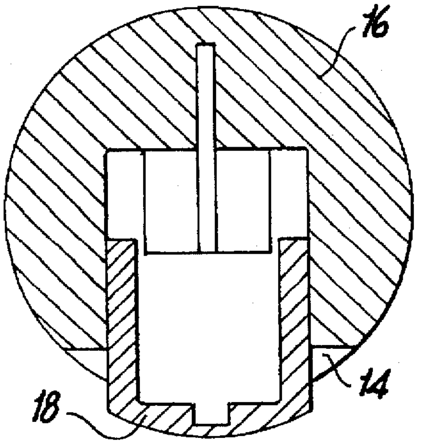
FIG. 11 is a front sectional view of the surgical instrument shown in FIG. 3, taken along line 11—11.
Figure 12:
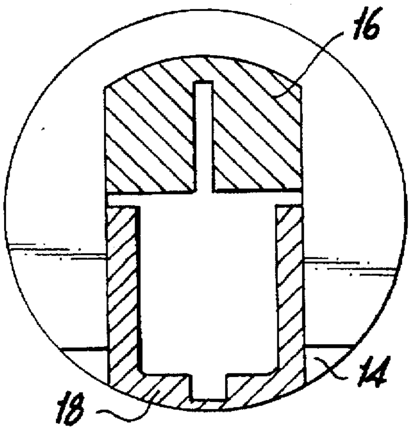
FIG. 12 is a front sectional view of the surgical instrument shown in FIG. 4, taken along line 12—12.

FIG. 3 shows the jaws in an intermediate spaced position (see also FIG. 11). By pulling on the actuating rod 68, the cam 46 is axially retracted from the first position A at the lower end 76 of the ramped slot to a second position B at an upper end 78 of the ramped slot. During the axial retraction, the cam 46 engages the diagonally extending camming surface 58 of the ramped slot to cause the lower jaw to pivot in a clockwise direction about the collar pin 28 with respect to the upper jaw. Jaw motion takes place rapidly relative to the axial movement of the actuating rod. Preferably, movement of the jaws from the fully open position to the intermediate position is accomplished with little or no axial movement of the jaws relative to the tubular member. A high clamping force between the jaws is unnecessary at this stage of the operation because the jaws are only beginning to capture tissue between their tissue contacting surfaces. Notably, in the intermediate position, the collar pin 28 is still located near the distal end 72 of the collar arm slots 26 and the cam 46 still engages the lower camming surface 48 of the upper jaw. Further, the lower jaw has moved into a position wherein further axial movement of the lower jaw will cause the curved upper portion 64 of the ramp 62 to contact a lower edge 70 of the opening 23 of the collar (see also FIGS. 1 and 10). It is the interaction between the ramp and the collar that will cause the jaws to approximate in a substantially parallel relation.

FIG. 4 shows the jaws in an approximated position wherein the cam 46 has been pulled from the second position B to a third position C. During the axial retraction, the cam 46 engages the upper end of the ramped slot 56 which acts as a cam stop 80, forcing the lower jaw and, correspondingly, the upper jaw (through the connection at the collar pin 28) to retract axially into the tubular frame. Axial retraction also causes the jaws to approximate due to engagement of the ramp 62 with the lower edge 70 of the opening of the collar (see also FIG. 12).

During the approximating phase of operation, jaw movement takes place slowly in relation to actuating rod movement. High clamping forces are desired at this point due to the high force required to compress the tissue captured between the jaws. High force multiplication occurs as the ramp 62 bears against the lower edge of the opening of the collar 14. Notably, in the approximated position, the collar pin 28 has moved to a proximal end 82 of the collar arm slots 26 and the jaws are fully retracted into the collar, with the collar contacting the shoulder 66 on the lower jaw adjacent the lower end of the ramp 62.

It will be appreciated that the above described construction enables the jaws of the instrument to open widely with relatively little extension of the jaws beyond the end portion 22 of the collar 14 (as shown by the vertically oriented dashed line L at the left end of FIGS. 2–4). This result is achieved by dividing the jaw closure action into two parts: a first part, wherein the actuating rod moves the cam from position A to position B, which requires very little, if any, axial movement of the jaws and, a second part, wherein the actuating rod moves the cam from position B to position C, which does require axial movement of the jaws. Notably, the second part of the jaw closure action is limited to the segment where high forces are required to compress the captured tissue between the jaws. It will also be appreciated that the jaws are held substantially parallel over a significant portion of their operating range, and, in particular, between their intermediate and approximated positions.

In the preferred embodiment, the ramped slots 56 of the lower jaw have a triangular or a quadrilateral shape. This permits the lower jaw to move vertically or to rotate relative to the cam 46, without requiring actuation of the actuating rod by the operator.

Figures 13, 14, 15:
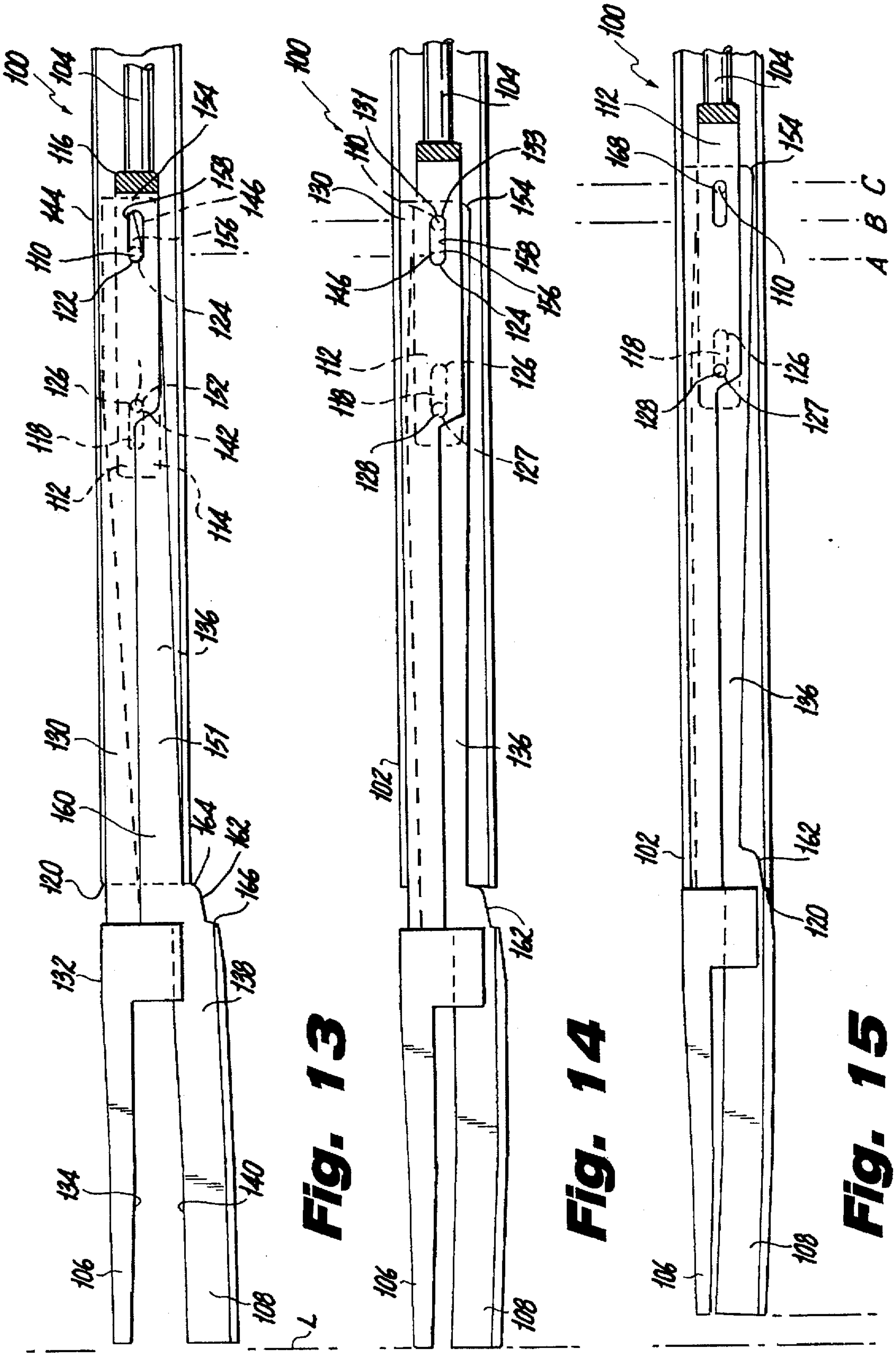
FIG. 13 is a side view of a first modified surgical instrument having an articulated jaw structure showing the jaws in a fully open position.
FIG. 14 is a side view of the surgical instrument shown in FIG. 13, showing the jaws in an intermediate position.
FIG. 15 is a side view of the surgical instrument shown in FIG. 13, showing the jaws in an approximated position.

With reference now to FIGS. 13–15, a first modified embodiment 100 of the surgical instrument is shown having a tubular frame 102, an actuating rod 104, an upper jaw 106 and a lower jaw 108. In this embodiment, the collar has been omitted and an elongated clevis 112 has been fixed to the distal end of the actuating rod 104. The clevis has a distal portion 114 and a proximal portion 116. The distal portion 114 defines an axially extending slot 118 for locating a clevis pin 128 such that the clevis pin extends transversely across the tubular frame 102. A cam 110, in the form of a pin, is fixably mounted to the proximal portion 116 of the clevis such that it is disposed parallel to the clevis pin 128 and transversely across the tubular frame.

The upper jaw 106 has a proximal portion 130 received in the tubular frame 102 and a distal portion 132 that extends out of a distal end 120 of the tubular frame. The distal portion of the upper jaw has a tissue contacting surface 134. Similarly, the lower jaw 108 has a proximal portion 136 received in the tubular frame and a distal portion 138 that extends out from the distal end of the tubular frame. The distal portion of the lower jaw has a tissue contacting surface 140.

The jaws are pivotally mounted to each other such that in an approximated position (FIG. 15), the tissue contacting surfaces are in opposed relationship to each other. The proximal portion 130 of the upper jaw 106 is a longitudinally extending bar that defines a traverse opening 142 for closely receiving the clevis pin 128. A proximal end 144 of the upper jaw defines an axially extending slot 146 that receives the cam 110. The slot 146 is horizontally disposed in FIGS. 13–15.

The proximal portion 136 of the lower jaw 108 is a pair of longitudinally extending members 151 that are located on each side, respectively, of the proximal portion 130 of the upper jaw. Each longitudinally extending member 151 defines a transverse opening 152 for closely receiving the clevis pin 128. The clevis pin 128 provides an axis about which the lower jaw may pivot with respect to the upper jaw. A proximal end 154 of each member 151 of the lower jaw defines a ramped slot 156 that receives the cam 110. The cam engages camming surfaces 158 of the ramp slots. In FIG. 13, the camming surface extends downwardly from the proximal end of the slot to the distal end of the slot. Each of the members 151 of the lower jaw also defines a ramp 162 at a distal end 160 thereof. An upper portion 164 of each ramp is curved. Below each ramp is a shoulder 166.

FIG. 13 shows the jaws in a fully open position with the cam 110 in a first position A and the distal portions 132, 138 of the jaws fully extended from end 120 of the tubular frame 102. The cam 110 is at a distal end 122 of the upper jaw slot 146 and at a distal end 124 of the ramped slot of the lower law 156, preventing counterclockwise rotation of the lower jaw about the clevis pin 128. The clevis pin 128 is in a first position at a proximal end 126 of the clevis slot 118. Upper surfaces on the proximal portions of both jaws may be configured to contact the interior surface of the tubular frame.

FIG. 14 shows the jaws in an intermediate spaced position wherein the cam 110 has been pulled from the first position A at the distal end 124 of the ramped slot 156 of the lower jaw to a second position B at a proximal end 131 of the ramped slot. During the axially retraction, the cam 110 engages the camming surface 158 of the ramped slot to cause the lower jaw to clevis pin 128 clevis pin 128 in a clockwise direction with respect to the upper jaw. Notably, in the intermediate position, the clevis pin 128 is now located at a distal end 127 of the clevis slot 118 and the cam 110 is located at a proximal end 133 of the upper jaw slot.146, it being appreciated that the upper and lower jaw slots are now horizontally aligned.

FIG. 15 shows the jaws in an approximated position wherein the cam 110 has been pulled from the second position B to the third position C. During the axial retraction, the cam engages both slot ends of the upper and lower jaw slots, the slot ends acting as a cam stop 168, forcing the jaws to retract axially into the tubular frame. Axial retraction further causes the jaws to approximate due to engagement of the ramp 162 with the end 120 of the tubular frame. The lower jaw may also be permitted to rotate about the cam 110 during retraction. Notably, in the approximated position, the clevis pin 128 is still located at the distal end 127 of the clevis slot 118. It will be appreciated that the operation and benefits of the present embodiment are generally similar to that of the previously described embodiment.

Figure 16:
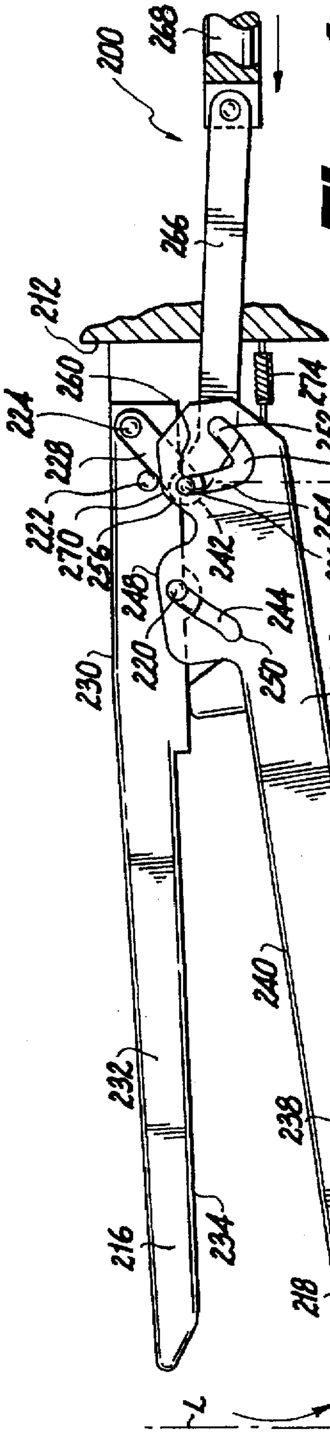
FIG. 16 is a side view of a second modified surgical instrument having an articulated jaw structure, showing the jaws in a fully open position.
Figure 17:
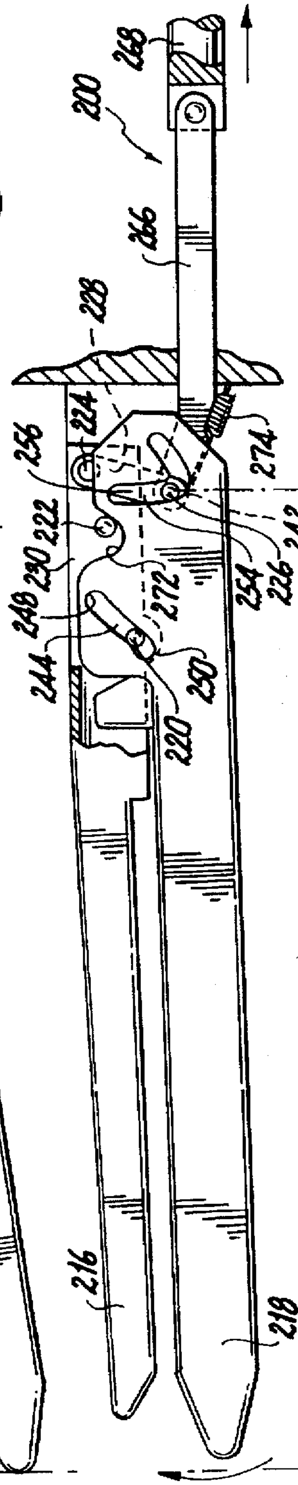
FIG. 17 is a side view of the surgical instrument shown in FIG. 16, showing the jaws in an intermediate position.
Figure 18:
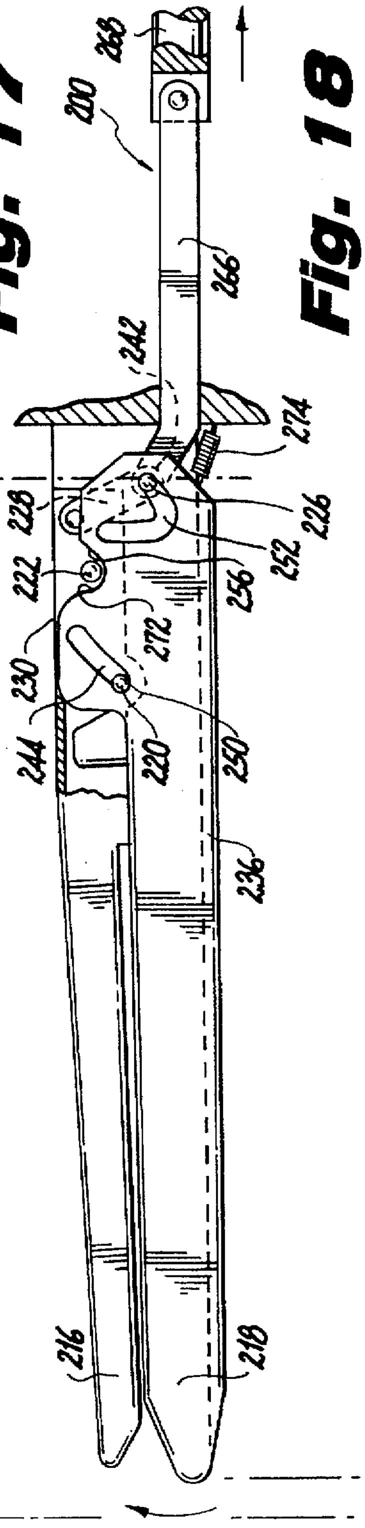
FIG. 18 is a side view of the surgical instrument shown in FIG. 16, showing the jaws in an approximated position.

With reference now to FIGS. 16–18, a second modified embodiment 200 of the present invention is shown wherein only one of the jaws is axially movable. The surgical instrument includes a frame member 212, an upper jaw 216 and a U-shaped lower jaw 218. The upper jaw has a proximal portion 230 fixably mounted to the frame member and a distal portion 232 having a tissue contacting surface 234. The lower jaw 218 has a proximal portion 236 mounted to the upper jaw and a distal portion 238 having a tissue contacting surface 240. The jaws are pivotally mounted to each other such that in an approximated position (FIG. 18), the tissue contacting surfaces of the jaws are in opposed relationship to each other.

The proximal portion 230 of the upper jaw includes an articulating mechanism for opening and closing the jaws. In particular, the proximal portion defines three pins arranged parallel to each other and which protrude transversely from each side of the upper jaw, a first pin 220, a cam pin 222 and a pivot pin 224. A link 228 is pivotally mounted to the pivot pin 224 on each side of the upper jaw. As the link on each side of the jaw is identical, only one will be described. A distal end 242 of the link is provided with a link pin 226 that is parallel to the other pins and extends outwardly from the link. It will be appreciated that there is a space between the links for receiving a knife actuating assembly, as more fully described in connection with FIG. 19.

The proximal portion 236 of the lower jaw has an articulating mechanism that corresponds to the articulating mechanism of the upper jaw. In the preferred embodiment, both upstanding walls of the U-shaped lower jaw have identical corresponding articulating structure at the proximal portions, namely, a first slot 244 for receiving the first pin 220 of the upper jaw and a second slot 246 for receiving the link pin 226 located at the distal end of the link 228. The first slot 244 extends diagonally downward from a proximal end 248 to a distal end 250. The second slot 246 has two portions, a proximal portion 252 having a mild slope relative to the longitudinal axis of the lower jaw and a distal portion 254 having a steep slope that is preferably disposed at an angle greater than 90° relative to the longitudinal axis of the lower jaw. The proximal portion of the lower jaw further includes a cam surface 256 for engaging the cam pin 222 of the upper jaw. The cam surface extends diagonally upward towards the proximal end of the lower jaw.

The distal ends of the links 228 may be mounted to a clevis 266 of an actuating rod 268 which is axially movable. Preferably, the clevis is pivotally mounted to the actuating rod about a traverse axis parallel to the pins 220, 222, 224, 226. A proximal end (not shown) of the actuating rod is connected to the surgical instrument by methods known to those skilled in the art for actuation by the operator of the instrument. The link pin 226 is movable between first, second and third positions to be described below in more detail.

The operation of the jaw structure of the second modified embodiment will now be described. FIG. 16 shows the jaws in a fully open position with the link pin 226 in a first position A and the lower jaw extended distally relative to the upper jaw. The first pin 220 is in a first position at the proximal end 248 of the first slot 244 whereas the link pin 226 is at an upper end 260 of the distal portion 254 of the second slot. The cam pin 222 is at an upper end 270 of the cam surface 256.

FIG. 17 shows the jaws in an intermediate spaced position wherein the link pin 226 has been pulled by the actuating rod from the first position A to a second position B. During the axial retraction, the link 228 rotates in a counterclockwise direction causing the link pin 226 to ride down the distal portion 254 of the second slot, pulling the lower jaw proximally. It is this axial linear motion of the lower jaw that pulls tissue into the gap between the jaws and inhibits tissue from extruding out of the gap during approximation. In addition to the axial motion, the lower jaw also draws closer to the upper jaw due to its rotation about the link pin 226 as the first pin 220 slides from a first position at the proximal end 248 of the first slot to a second position near the distal end 250 of the first slot. Jaw motion from the open position to the intermediate position, takes place rapidly relative to actuating rod movement. A high clamping force is unnecessary at this stage of the operation because the jaws are only beginning to capture tissue. Notably, in the intermediate position, the cam pin 222 is at a lower end 272 of the cam surface 256.

FIG. 18 shows the jaws in an approximated position wherein the link pin 226 has been pulled by the actuating rod from the second position B to a third position C. During the axial retraction, the link pin 226 rides up the proximal portion 252 of the second slot, causing the lower jaw to close further as it rotates about the first pin 220. During this phase of the operation, jaw motion takes place slowly in relation to actuating rod movement. High clamping force is desired due to the high force required to compress the captured tissue between the jaws. Notably, in the approximated position, the first pin 220 moves to the distal end 250 of the first slot and the cam pin 222 remains at the lower end 272 of the cam surface 256.

It will be appreciated that the cam pin 222 is particularly useful for reopening the jaw structure. In moving from the approximated position to the intermediate position, the cam pin 222 will engage the cam surface 256 to urge the lower jaw to its fully open, extended position. A biasing mechanism, such as a spring 274, may be connected between the proximal portion 236 of the lower jaw and the frame 212 to urge the lower jaw from its fully open position to the intermediate position (see FIG. 16).

As with the previously described embodiments, the second modified embodiment enables the jaws of the instrument to open widely with relatively little extension of the jaws beyond the end of the frame. Furthermore, the jaws are held substantially parallel over a significant portion of their opening range and, in particular, between their intermediate and approximated positions.

With reference to FIGS. 20 and 21, a third modified embodiment 300 of the present invention is shown. As with the second modified embodiment, an upper jaw 310 has a proximal portion 312 that includes an articulating mechanism for operating the jaws. The proximal portion includes a collar 314 defining a longitudinally extending opening 316 at the center thereof. A first pin 320 is mounted to the collar transversely across the longitudinally extending opening 316. A cam pin 322, parallel to the first pin 320, extends outwardly from each side of the collar. A pivot pin 324, parallel to the first pin and the cam pin, extends outwardly from each side of the proximal portion of the upper jaw, adjacent the collar. A link 328 is pivotally mounted to each side of the upper jaw at the pivot pin 324. A distal end 329 of each link is provided with a link pin 326 that is parallel to the other pins and extends outwardly from its respective link.

A U-shaped lower jaw 330 includes a base wall 332 and two upwardly extending side walls 334. In addition, the lower jaw is provided with an interior cam plate 336 that is disposed in the longitudinally extending opening 316 of the upper jaw. A mounting block or blocks 350 may be used to mount the cam plate 336 to the upwardly extending side wall(s) of the lower jaw. The mounting blocks may be placed between the sides of the cam plate and each of the upwardly extending walls, just below the lower surface of the upper jaw. As in the second modified embodiment, a first slot 338 is provided for engaging the first pin 320, a second slot 340 is provided for engaging the link pin 326 and a cam surface 342 is provided for engaging the cam pin 322. In this instance, however, the first slot 338 is disposed in the interior cam plate 336 of the lower jaw, not in the upwardly extending walls. In this regard, it will appreciated that the operation of the jaws of the third embodiment, between the fully opened, the intermediate and the approximated positions is similar to that fully described in connection with the second modified embodiment and need not be further described.

With reference now to FIGS. 1 and 4, the surgical instrument, in this case, a surgical stapling apparatus, is shown having a knife assembly 510 mounted in the disposable staple cartridge 508 for longitudinally slidable movement therein. The construction of the staple cartridge and the techniques for operating the stapling mechanism are well known to those skilled in the art. Briefly, however, the staple cartridge is typically a longitudinally extending member that is detachably mounted within the U-shaped lower jaw 18 of the surgical instrument. The staple cartridge includes a longitudinal slit 514 and a number of slots 516 arranged on both sides of the slit and adapted to accommodate staples 518 and staple pushers 520 (see also FIG. 27). The upper jaw or anvil jaw 16 of the surgical stapler typically includes a longitudinal slit (not shown) aligned with the slit 514 of the staple cartridge when the jaws are in the approximated position and also includes a plurality of rows of depressions 523 aligned with the staple slots 516 for bending the staples fired from the staple cartridge. To eject the staples, a plurality of pusher rods 524, pointed at their distal ends 526 are inserted through additional slits 528 in the proximal end of the staple cartridge (see FIGS. 23 and 24) to slide longitudinally therein. The pusher rods contact the pushers 520, causing the pushers to rise and expelling the staples 518 out of their slots (FIG. 27). Tissue 529 captured between the jaws is thus stapled and cut.

With reference now to FIGS. 22A–H, the knife assembly 510 is shown mounted in the staple cartridge. The knife assembly includes a longitudinally extending knife support 530 having a proximal end 532 and a distal end 534 and a knife blade 536 defining a cutting edge 538. The knife blade extends upwardly from the support with its cutting edge facing distally. With reference to FIG. 26, the knife blade includes an integral base 540 that may be seated in a notched area 542 at the bottom of the knife support with the cutting edge of the blade protruding through an opening 544 at the top of the knife support.

The proximal end 532 of the knife support includes a pair of latch receivers 546 extending transversely from each side of the knife support. Each latch receiver may be configured as a trapezoid having a proximally located, upwardly extending, ramp 548 and a distally located, downwardly extending, ramp 550.

The knife assembly is received in a longitudinally extending opening of the staple cartridge, with the knife blade extending upwardly through the longitudinal slit 514 of the staple cartridge. The knife blade is initially disposed in a protective shield 551 at the proximal end of the staple cartridge. The bottom of the staple cartridge includes a recessed portion 553 and a trough portion 554 for receiving the knife support 530 of the knife assembly (See FIG. 24). The recessed portion 553 closely receives the knife support, whereas the trough portion 554 defines a tunnel 552 on each side of the knife support, the purpose of which will be described in more detail below in connection with the operation of the knife actuating assembly. The additional slits 528 shown in FIG. 24 are for receiving the pusher rods 524 previously described.

A knife actuating assembly 512 for moving the knife is also shown in FIGS. 22A–H. The knife actuating assembly includes a base 556, a blade support 558 and two latch assemblies 560. The blade support is preferably a metal blade that is fixedly centered on the top of the base and disposed in a longitudinal direction. The latch assemblies each include a flexible latch arm 562 having a proximal end 564 and a distal end 566. A latch 568 is disposed at the distal end of each latch arm. The proximal ends of the latch arms are fixedly mounted within a recess 570 at the bottom of the base. The recess includes a beveled portion 572 at the distal end of the base to permit the latch arms to deflect upwardly. The proximal end (not shown) of the knife actuating assembly is connected to the surgical instrument by methods known to those skilled in the art for actuation by the operator of the instrument. The knife actuating assembly is movable between a first latched position, a second latched and an unlatched position, as will be described in more detail below.

Figure 5:
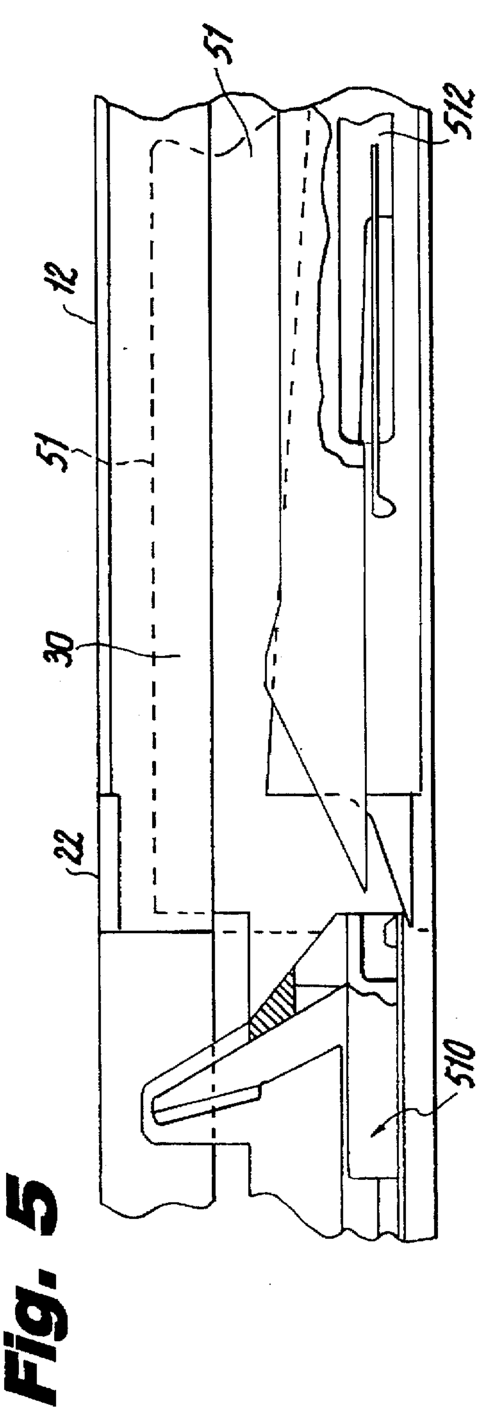
FIG. 5 is an enlarged side view of the knife assembly and the knife actuating assembly of the surgical instrument shown in FIG. 4.

Preferably, the pusher rods 524 are also mounted to the knife actuating assembly to ensure that the pusher rods and the knife blade 536 move simultaneously in a predetermined manner through the staple cartridge during the stapling/cutting procedure. With reference to FIGS. 4 and 5, the knife assembly 510 and the knife actuating assembly 512 are shown located in the first embodiment of the invention. The staple cartridge and knife assembly 510 form an integral disposable part that is located in the distal portion of the lower jaw (see FIG. 1). The knife actuating assembly is located in the tubular frame 12 between the longitudinally extending members 51 of the lower jaw. The blade support 558 and pusher rods 524 are located below the proximal portion 30 of the upper jaw. Alternatively, the proximal portion of the upper jaw may be configured to permit free movement of the blade support and pusher rods longitudinally through the tubular frame. Notably, when the jaws are in the fully open and intermediate positions, the knife assembly typically cannot be operated because it is out of alignment with the knife actuating assembly. In the approximated position (FIGS. 4 and 5), the knife assembly and knife actuating assembly are aligned. In this position, the staple cartridge is ready to be fired and the knife is ready to be actuated to cut through tissue captured between the jaws.

With reference to FIG. 19, the second modified embodiment is similarly shown having the knife assembly 510 and knife actuating assembly 512 located in the surgical instrument. The knife assembly is located in the distal portion 238 of the lower jaw and the knife actuating assembly is located at the bottom of the proximal portion 236 of the lower jaw between the links 228. The blade support 558 and pusher rods 524 are located below the proximal portion 230 of the upper jaw. As with the first embodiment shown in FIG. 5, the knife assembly typically cannot be operated when the jaws are in the open and intermediate positions (FIGS. 16 and 17), but is operable in the approximated position (FIG. 18).

With reference now to FIG. 23, the knife actuating assembly 512 is shown initially engaged to the knife assembly 510 and staple cartridge 508. In particular, the pusher rods 524 are located by the slits 528, which have beveled outer edges 574 to facilitate entry. The blade support 558 is located by a shallow slit 576 formed into the upper surface of the knife support 530 (See also FIGS. 24 and 26). The shallow slit may also be beveled to facility entry of the blade support.

Figure 22A:
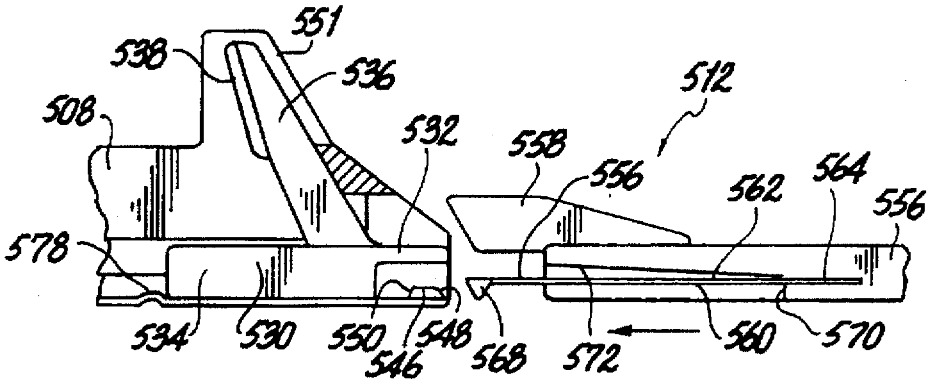
FIGS. 22A–H are enlarged sectional views of a knife assembly and a knife actuating assembly, wherein the assemblies are shown at various stages of operation in a surgical instrument.
Figure 22B:
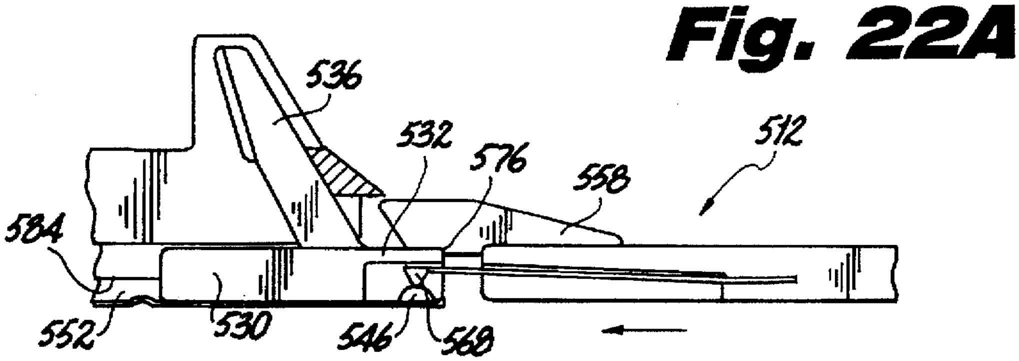
Figure 22C:
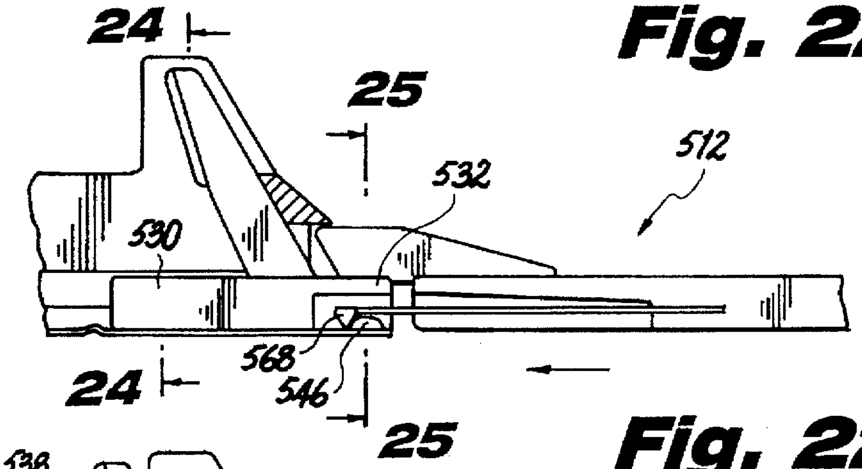

With reference now to FIGS. 22A–22H the operation of the knife actuating assembly will be described. FIG. 22A shows the knife actuating assembly in an unlatched position wherein the latch 568 and the blade support 558 are out of contact with the staple cartridge 508 and knife assembly 510. FIG. 22B shows a prelatched position, with the knife actuating assembly moved from right to left as shown by the arrow. The blade support 558 is located in the shallow slit 576 at the top of the knife support 530 and the latch receiver 546 has deflected the latch 568 upwardly as the latch rides up the ramp 548. Notably, the knife assembly has not moved forward yet, despite the horizontal component of force applied by the latch to the latch receiver, because a detent 578 integral with the bottom of the cartridge offers adequate resistance to forward motion at this point. FIG. 22C shows a first latched position at the proximal end of the cartridge, wherein the latch has dropped behind the latch receiver (see also FIG. 25 showing the latch arms 562 disposed over the latch receivers 546).

Figure 22D:
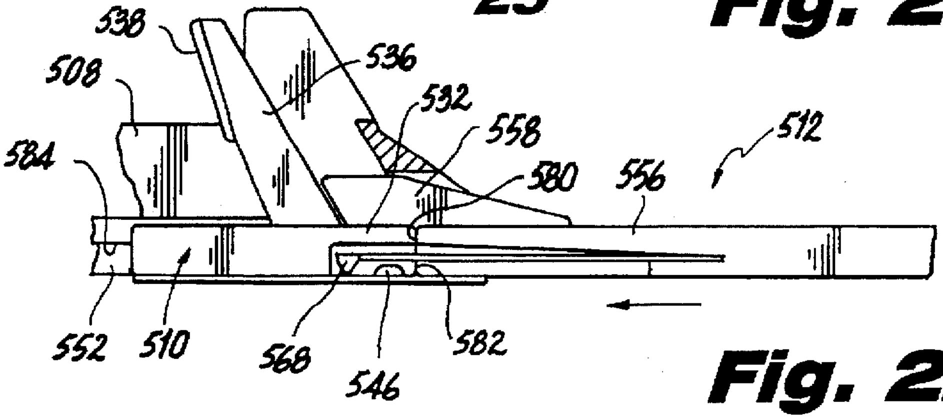

FIG. 22D shows the knife actuating assembly in a firing position, wherein a bearing surface 580 of the base 556 contacts a bearing surface 582 at the proximal end 532 of the knife assembly and starts pushing the knife assembly forward, overcoming the resistance of the detent. Notably, the blade support 558 does not quite contact the back surface of the knife blade 536, its purpose being to act as a support in case the resistance to cutting is so great that the knife assembly tends to tilt backwards. It should also be appreciated, that the latches 568 of the knife actuating assembly are engaged in the tunnels 552 located on each side of the knife support 530 of the knife assembly, at the bottom of the cartridge (see FIG. 24). The location of the latches in the tunnels becomes important when it is time to withdraw the knife, because a roof 584 of each tunnel will ensure that the latches cannot disengage from the latch receivers until the knife is fully retracted.

Figure 22E:
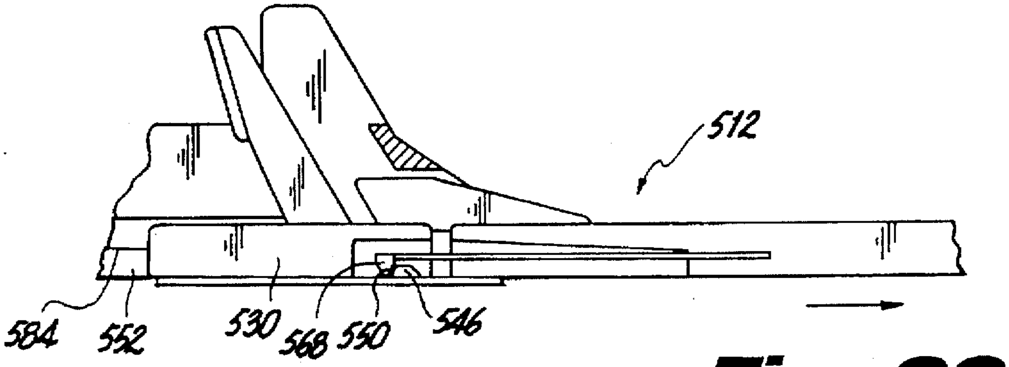
Figure 22F:
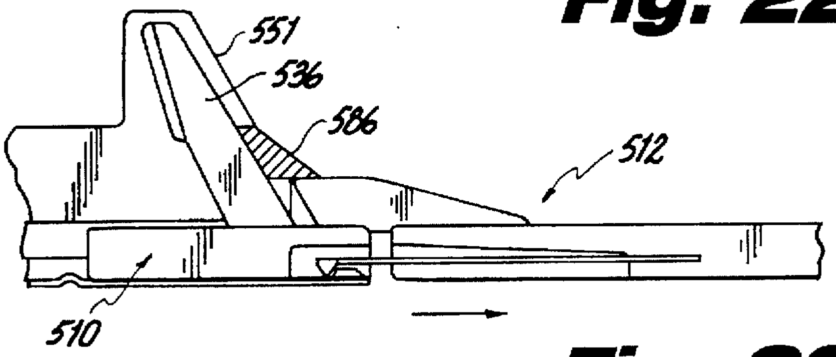
Figure 22G:
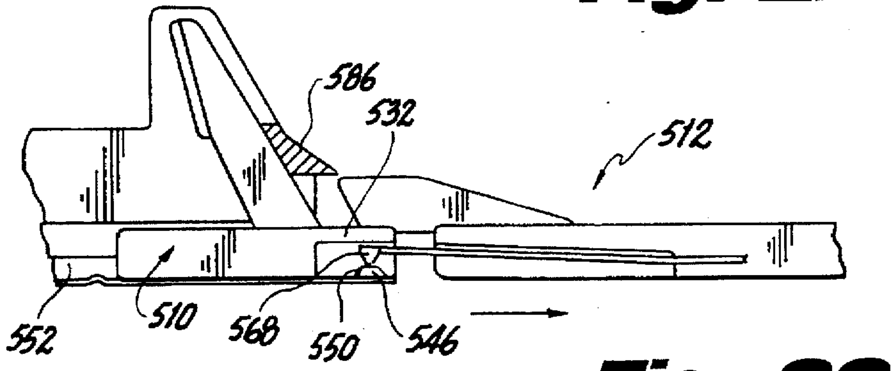
Figure 22H:
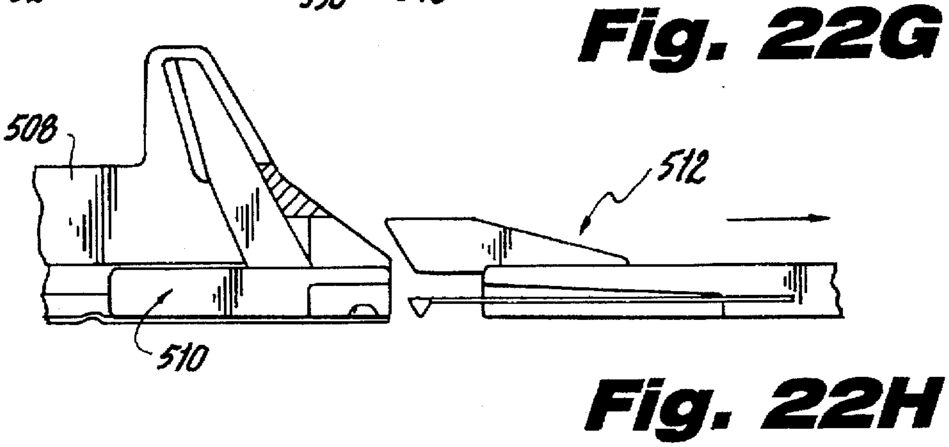

FIG. 22E shows the knife assembly in a second latched position wherein the knife actuating assembly withdraws the knife assembly from left to right as shown by the arrow. In this position, the latch 568 engages the distally located ramp 550 of the latch receiver 546. The roof 584 of the tunnel 552 prevents removal of the latch, thus the latch is able to pull the knife assembly through the longitudinal slit. FIG. 22F shows a stopped position wherein the knife actuating assembly has pulled the knife assembly back as far as it will go. A rib 586, formed as an integral part of the cartridge, does not allow the knife blade 536 to retract any further. FIG. 22G is a disengaged position wherein the latch receiver 546 has deflected the latch 568 upwardly as the latch rides up the distally located ramp 550. Notably, the proximal end 532 of the knife support 530 has emerged from the tunnels 552 at this point (see also FIG. 23) and the latch 568 is free to deflect upwardly. Since the knife assembly is held in position by the rib 586, the knife actuating assembly continues to move backwards (left to right) and disengages from the knife assembly which remains in the cartridge, as shown in FIG. 22H.

The knife assembly may be an integral part of the disposable staple cartridge and may also be a reusable knife actuating assembly which stays with the reusable instrument. The knife actuating assembly includes a latch that is captured by a latch receiver in the knife assembly. As the knife actuating assembly moves forward, it bears against with the knife assembly and moves the knife forward to cut the tissue captured between the jaws. The knife assembly stays engaged to the knife actuating assembly as the latter is retracted until the knife assembly reaches its starting position, at which point the two assemblies unlatch and the knife actuating assembly is free to be further retracted out of the disposable staple cartridge.

The knife assembly eliminates the need for a rigid connection between the knife and its actuating mechanism. This permits the cartridge jaw to be articulated near the point where the knife connects with its actuating mechanism. Articulation at this location frees the jaw from simply rotating about a single pivot point and offers an opportunity to implement near-parallel jaw closure. The invention is particularly suitable in endoscopic or laparoscopic procedures wherein it is desired that the jaws open widely in an essentially parallel relationship while at the same time extending minimally beyond the end of the tubular frame of the surgical instrument.

Figure 28:
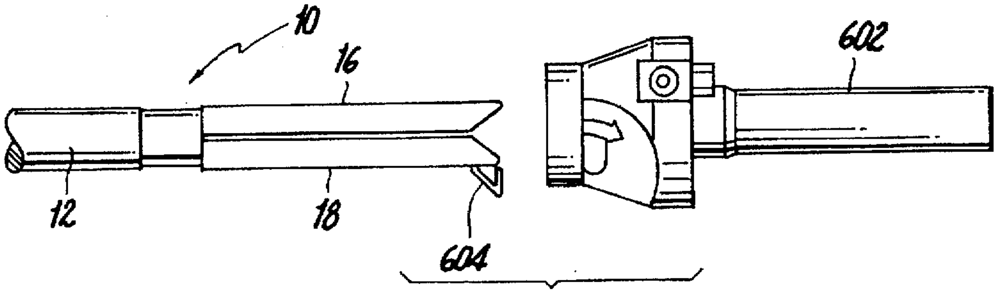
FIG. 28 is a side view of a portion of a laparoscopic stapler with a blocking body according to the present invention and a trocar cannula, which illustrates the blocking body in a blocking position.
Figure 29:
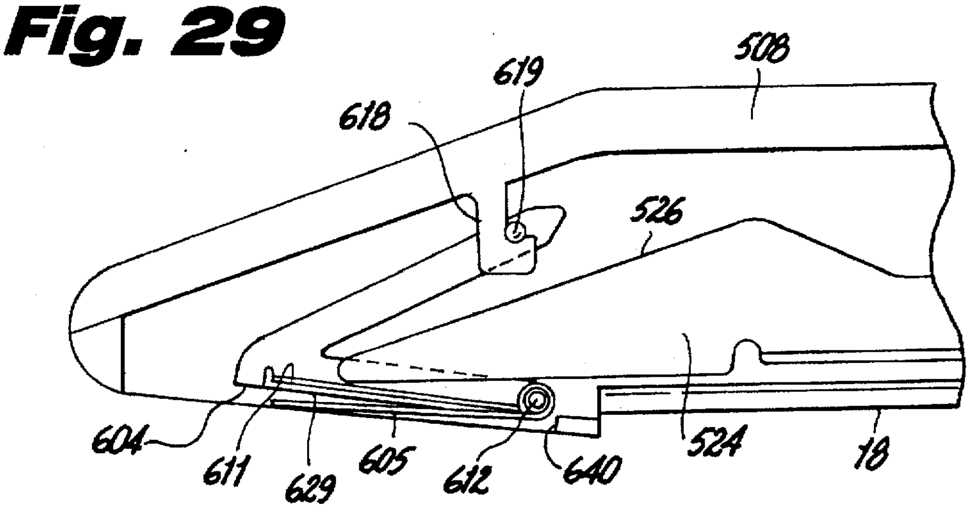
Figure 30:
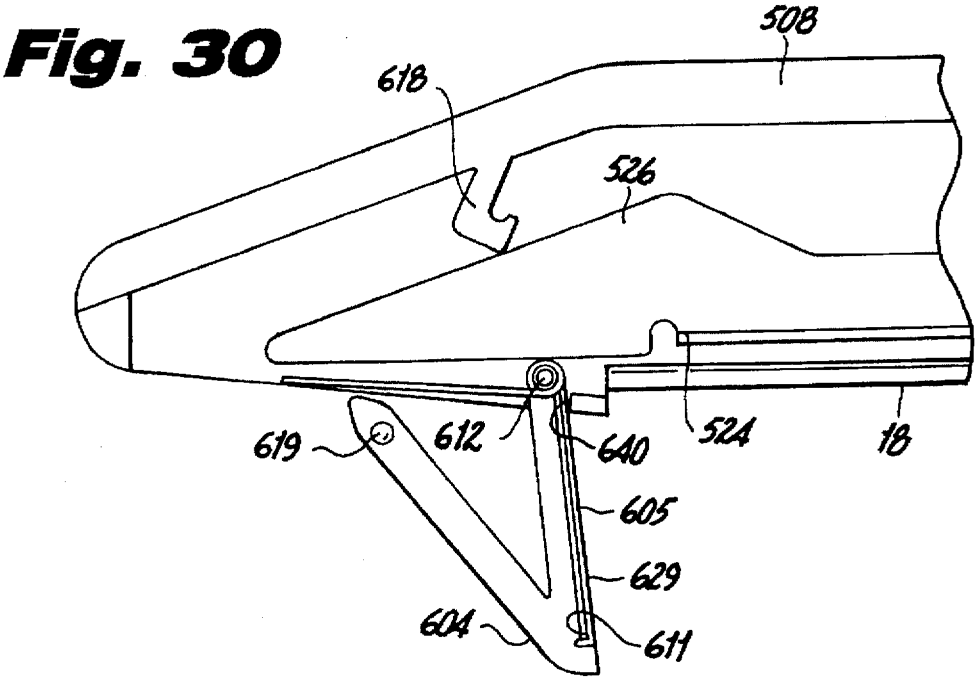

Referring now to FIGS. 28 through 30 of the drawing, there is shown a preferred embodiment of laparoscopic surgical instrument according to the present invention which includes many of the same elements of the devices discussed above which have been identified by the same reference characters.

According to the present invention there is provided a laparoscopic surgical instrument such as the stapler 10 that is adapted to be inserted (or "threaded") through a cannula 602 (FIG. 28) and into the abdominal cavity of a patient during a laparoscopic surgical procedure.

The present invention comprises a laparoscopic surgical instrument (e.g. the stapler 10) which includes at least one mechanical tissue engagement device (e.g. staples 518). While a stapler 10 is used as a particular example, as used in this application, the phrase "laparoscopic surgical instrument" should be construed broadly to include clip appliers, tissue tackers and other surgical instruments. Additionally, while staples 518 are used as an example of a mechanical tissue engagement device, as used in this application, the phrase "mechanical tissue engagement device" should also be construed broadly to include surgical clips, patches, tissue tackers, and one-piece and two-piece staples.

The stapler 10 comprises a proximal portion, a distal portion having staples 518, an actuation means for placing the staples 518 on tissue, an elongate, substantially cylindrical shaft portion or frame 12 between the proximal and distal portions for abutment with inner surfaces of the cannula 602 when the stapler 10 is within the cannula 602, and a blocking body or member 604.

Preferably, the actuation means includes pusher rods 524 having distal ends 526 as discussed above. The blocking body 604 is operatively associated with the actuation means 524 as described below in greater detail. The blocking body 604 is preferably mounted to the cartridge 508 for pivotal movement relative thereto between a non-blocking position (FIG. 29) which affords insertion and removal of the distal portion of the stapler 10 through the cannula 602, and an insertion blocking position (FIGS. 28 and 30) in which the blocking body 604 affords removal of the distal portion from the abdominal cavity, and in which the blocking body 604 thereafter prevents insertion of the distal portion through the cannula 602.

The stapler 10 also preferably includes a biasing means such as a spring 605 for urging the blocking body 604 toward the blocking position. A ledge or shoulder surface 640 on the cartridge 508 functions as a stop surface to prevent further distal movement of the body 604 relative to the cartridge 508 and to define the insertion blocking position of the body 604. The spring 605 is illustrated as a torsion spring which has a first portion attached to the cartridge 508 and a second portion attached to a ledge 611 on the blocking body 604. However, it should be noted that the biasing means may comprise any suitable biasing means such as a coil spring, leaf spring or even an inherently resilient blocking body 604 which could press against the cartridge 508 to bias itself toward the insertion blocking position.

Also preferably, the blocking body 604 is pivotably mounted to the cartridge 508 by a pin 612 and a groove in the cartridge 508. A flexible, resilient latch 618 is also preferably present in the cartridge 508. The blocking body 604 has a pin 619 for engaging the latch 618 to hold the blocking body 604 in the non-blocking position, and a cam surface 629 for engaging the distal end of the cannula 602 to afford removal of the distal portion from the abdominal cavity through the cannula 602 even when the blocking body 604 is in the blocking position. The blocking body 604 also includes an obstruction surface 631 for engaging the cannula 602 to prevent the spent surgical instrument from being reinserted through the cannula 602.

With the blocking body 604 in the non-blocking position, the effective diameter of the distal portion of the stapler 10 is approximately equal to or less than the diameter of the internal surfaces of the cannula 602 which allows the distal portion to be inserted through the cannula 602. However, when the blocking body 604 is in the insertion blocking position (FIGS. 28 and 30), the effective diameter of the distal portion of the stapler 10 is greater than the diameter of the internal surfaces of the cannula 602, and the stapler 10 is prevented from being reinserted through the cannula 602.

It should be noted that when the blocking body 604 is in the abdominal cavity and assumes the insertion blocking position, it does not prevent the stapler 10 from being withdrawn from the cannula 602 as the cam surface 629 will engage the end of the cannula 602 as the distal portion of the stapler 10 is being withdrawn, and the cam surfaces 629 will cam the blocking body 604 toward the non-blocking position where it affords passage of the distal portion of the stapler 10 out of the cannula 602. Because the latch 618 is flexible and resilient, it will not unduly hinder this return movement of the blocking body 604 toward the non-blocking position as it simply deflects out of the path of pin 619.

The materials used to construct the elements of the cartridge 508 including the blocking body 604 and the spring 605 may comprise any suitable materials for use in surgical procedures. Polymeric and metal materials may be utilized. Stainless steel is a suitable material for the blocking body 604.

OPERATION

The present invention will now be described with reference to FIGS. 28 through 30. A surgeon will first place a cannula 602 in the abdominal cavity of a patient by using a trocar which is well known in the art. Next, the distal portion of the stapler 10 will be inserted into the abdominal cavity through the cannula 602. Typically the shaft 12 will abut the internal surfaces of the cannula 602 so that insufflation gas pressure will not be lost between the cannula 602 and shaft 12.

The surgeon will then approximate (e.g. place) the jaws of the stapler 10 on the tissue to be stapled, and the actuation means will be actuated (the stapler is fired). When the stapler is fired, the pusher rods 524 move distally along a path within slits 528 as described above until the supply of staples 518 is depleted and the cartridge is spent. As used in this application, when it is said that a laparoscopic surgical instrument is "spent" or that it is "depleted", it is meant that there are no mechanical tissue engagement devices (e.g. staples 518) remaining to be engaged on tissue.

At a distal end portion of the path which the pusher rod 524 follows, a distal end 526 of the pusher rod 524 engages flexible latch 618 and moves the latch from a latching position (FIG. 29) to an unlatched position (FIG. 30) where the pin 619 is spaced from the latch 618 so that the spring 605 may move the blocking body 604 to the insertion blocking position. Thus, the distal end 526 of pusher rod 524 is operatively associated with the latch 618. Preferably, engagement between the distal end 526 of the pusher rod and the latch 618 occurs during or just after the last staple or staples are being formed in tissue.

If there is no obstacle (such as tissue) obstructing the blocking body 604, the blocking body may project beyond the periphery of the cartridge 508 and move to the blocking position even when it is within the abdominal cavity. As stated above, engagement between cam surface 629 and the end of the cannula 602 as the stapler 10 is withdrawn from the abdominal cavity moves the blocking body 602 back toward the non-blocking position so that the stapler 10 may be withdrawn from the abdominal cavity.

Once the spent stapler 10 is removed from the abdominal cavity, if a surgeon attempts to reuse the stapler 10, engagement between blocking surface 631 and a proximal surface on the cannula 602 will prevent the stapler 10 from being reinserted into the abdominal cavity through the cannula. The shape of the blocking body 602 shown in FIG. 30 as including first and second portions situated at an included acute angle presents a blocking body in the insertion blocking position which is difficult to reset as the blocking surface 631 is situated at a predetermined angle relative to the cannula 602 such that it acts as a camming surface to urge the stapler away from the passage of the cannula 602 should the surgeon attempt to force it through the cannula 602. Thus, the blocking body 604 allows the spent surgical instrument to be removed from the abdominal cavity through the cannula, but thereafter prevents the instrument from being reinserted through the cannula. Valuable time is not wasted by inserting a spent instrument through the cannula, and tissue is not unnecessarily traumatized.

It will, of course, be understood that modifications to the presently preferred embodiment will be apparent to those skilled in the art. For example, the blocking body 604 need not comprise the V-shape shown in FIGS. 29–30, and may comprise any suitable shape so long as it performs the functions described above. Consequently, the scope of the present invention should not be limited by the particular embodiments discussed above, but should be defined only by the claims set forth below and equivalents thereof.

We claim:

1. A laparoscopic surgical procedure comprising the steps of:

providing a cannula, inserting a portion of the cannula into the abdominal cavity of a patient, providing a laparoscopic instrument having a distal portion including a first jaw and a second jaw with at least one mechanical tissue engagement device provided on at least one of the first and second jaws, an actuation means capable of engaging the mechanical tissue engagement device on tissue, and a blocking body movable between an insertion blocking position preventing insertion of the distal portion into the cannula and a non-blocking position allowing insertion of the distal portion into the cannula, inserting the distal portion of the laparoscopic surgical instrument with the blocking body in the non-blocking position into the abdominal cavity of the patient through the cannula, actuating the actuation means to release the at least one mechanical tissue engagement device from the first or second jaw until no mechanical tissue engagement device remains to be engaged on tissue, moving the blocking body from the non-blocking position toward the insertion blocking position; and removing the distal portion from the abdominal cavity through the cannula.

2. The laparoscopic surgical procedure of claim 6 further comprising the step of:

biasing the blocking body toward the insertion blocking position; and restraining the blocking body against the bias during the step of inserting the distal portion.

3. The laparoscopic surgical procedure of claim 2, wherein the step of actuating includes the step of releasing the blocking body from being restrained.

4. The laparoscopic surgical procedure of claim 2 wherein the step of restraining the blocking body includes the step of releasably engaging a portion of the blocking body with a latch positioned within the distal portion.

5. The laparoscopic surgical procedure of claim 4 wherein the step of actuating includes the step of disengaging the portion of the blocking body from the latch.

6. The laparoscopic surgical procedure of claim 1 wherein the step of removing includes the step of engaging a camming surface of the blocking body with a distal end of the cannula to move the blocking body toward the non-blocking position during the removal of the distal portion through the cannula and thereafter biasing the blocking body to the insertion blocking position.

7. The laparoscopic surgical procedure of claim 1 further comprising the step of moving the first jaw and the second jaw to an approximated position prior to the step of removing the distal portion from the abdominal cavity.

8. A laparoscopic surgical procedure comprising the steps of:

providing a cannula, inserting a portion of the cannula into the abdominal cavity of a patient, providing a laparoscopic instrument having a distal portion with at least one mechanical tissue engagement device, an actuation means capable of engaging the mechanical tissue engagement device on tissue, and a blocking body movable between an insertion blocking position preventing insertion of the distal portion into the cannula and a non-blocking position allowing insertion of the distal portion into the cannula, inserting the distal portion of the laparoscopic surgical instrument with the blocking body in the non-blocking position into the abdominal cavity of the patient through the cannula, actuating the actuation means until no mechanical tissue engagement device remains to be engaged on tissue, moving the blocking body from the non-blocking position toward the insertion blocking position;

removing the distal portion from the abdominal cavity through the cannula including engaging a camming surface of the blocking body with a distal end of the cannula to move the blocking body toward the non-blocking position during the removal of the distal portion through the cannula and thereafter biasing the blocking body to the insertion blocking position, and engaging a blocking surface of the blocking body with a proximal end of the cannula to prevent reinsertion of the distal portion through the cannula.

9. A laparoscopic surgical procedure comprising the steps of:

providing a cannula, inserting a portion of the cannula into the abdominal cavity of a patient, providing a laparoscopic instrument having a distal portion with at least one mechanical tissue engagement device, an actuation means capable of engaging the mechanical tissue engagement device on tissue, a blocking body movable between an insertion blocking position preventing insertion of the distal portion into the cannula and a non-blocking position allowing insertion of the distal portion into the cannula, and a removable cartridge at the distal portion, the removable cartridge containing the at least one mechanical tissue engagement device, the blocking body being movably mounted to the cartridge, inserting the distal portion of the laparoscopic surgical instrument with the blocking body in the non-blocking position into the abdominal cavity of the patient through the cannula, actuating the actuation means until no mechanical tissue engagement device remains to be engaged on tissue, moving the blocking body from the non-blocking position toward the insertion blocking position; and removing the distal portion from the abdominal cavity through the cannula.

10. A surgical procedure comprising the steps of:

providing a cannula having an internal surface defining an inner cannula diameter;

inserting a portion of the cannula into a body cavity of a patient;

providing a surgical instrument having a distal portion with at least one releasable mechanical tissue engagement device provided on jaw structure associated with the distal portion, an actuation means capable of engaging the mechanical tissue engagement device on tissue, and a blocking body operatively associated with the distal portion and operable independent of the jaw structure, the blocking body movable between a non-blocking position wherein the distal portion has an effective diameter less than or equal to the inner cannula diameter and an insertion blocking position wherein the distal portion has an effective diameter greater than the inner cannula diameter;

inserting the distal portion of the surgical instrument with the blocking body in the non-blocking position through the cannula and into the body cavity of the patient;

actuating the actuation means to release the at least one releasable mechanical tissue engagement device;

removing the distal portion from the body cavity through the cannula; and moving the blocking body to the insertion blocking position.

* * * * *